United States Patent
Urvoy et al.

(10) Patent No.: US 11,589,940 B2
(45) Date of Patent: Feb. 28, 2023

(54) SURGICAL SYSTEM AND METHOD FOR TRIGGERING A POSITION CHANGE OF A ROBOTIC DEVICE

(71) Applicant: DePuy Ireland Unlimited Company, Ringaskiddy (IE)

(72) Inventors: François Urvoy, Gieres (FR); Andrew Burton, Raynham, MA (US); Nicolas Demanget, Gieres (FR); Daniel Girardeau-Montaut, Gieres (FR)

(73) Assignee: DePuy Ireland Unlimited Company, Ringaskiddy (IE)

( * ) Notice: Subject to any disclaimer, the term of this patent is extended or adjusted under 35 U.S.C. 154(b) by 287 days.

(21) Appl. No.: 16/951,532

(22) Filed: Nov. 18, 2020

(65) Prior Publication Data

US 2021/0169596 A1 Jun. 10, 2021

(30) Foreign Application Priority Data

Nov. 28, 2019 (EP) .................................... 19212185

(51) Int. Cl.
| | |
|---|---|
| *B25J 9/10* | (2006.01) |
| *A61B 34/00* | (2016.01) |
| *A61B 34/30* | (2016.01) |
| *B25J 9/16* | (2006.01) |
| *B25J 15/00* | (2006.01) |

(52) U.S. Cl.
CPC .............. *A61B 34/70* (2016.02); *A61B 34/30* (2016.02); *B25J 9/10* (2013.01); *B25J 9/1633* (2013.01); *B25J 15/0019* (2013.01)

(58) Field of Classification Search
CPC ..... A61B 17/1626; A61B 34/70; A61B 34/20; A61B 34/30; A61B 2034/2046;
(Continued)

(56) References Cited

U.S. PATENT DOCUMENTS

| | | | | |
|---|---|---|---|---|
| 6,587,750 B2 * | 7/2003 | Gerbi | ..................... | A61B 34/71 600/595 |
| 6,684,129 B2 * | 1/2004 | Salisbury, Jr. | ......... | A61B 34/30 600/595 |

(Continued)

FOREIGN PATENT DOCUMENTS

| | | |
|---|---|---|
| WO | 2006/091494 A1 | 8/2006 |
| WO | 2014/151550 A2 | 9/2014 |

OTHER PUBLICATIONS

Wilkening et al., Development and Experimental Evaluation of Concurrent Control of a Robotic Arm and Continuum Manipulator for Osteolytic Lesion Treatment, 2017, IEEE, p. 1625-1631 (Year: 2017).*

(Continued)

*Primary Examiner* — McDieunel Marc
(74) *Attorney, Agent, or Firm* — Condo Roccia Koptiw LLP

(57) ABSTRACT

The present disclosure relates to a surgical system for treating an anatomical structure according to a plurality of target planes and/or axes, comprising:
  a robotic device (1) comprising:
    an end effector (2) defining a current plane or axis,
    an actuation unit (11) coupled to the end effector (2),
  a tracking unit (3) configured to determine a pose of the current plane or axis,
  a control unit coupled to the tracking unit and configured to control the actuation unit (11) to align the current plane or axis of the end effector (2) with each one of the plurality of target planes and/or axes to treat the anatomical structure,
  the robotic device being operable in at least the following modes:
  a working mode wherein a treatment is being performed with the end effector constrained to one target plane or axis by the actuation unit, and (Continued)

a waiting mode wherein no treatment is being performed and the actuation unit is operable to move the end effector in alignment with another target plane or axis, wherein the control unit is further configured to:
(a) determine that the robotic device (1) is in the waiting mode;
(b) detect a triggering force applied to the end effector (2) and/or the actuation unit (11) in at least one first direction;
(c) as a result of determination (a) and detection (b), trigger a position change of the end effector (2) by the actuation unit (11) to align the current plane or axis with a next target plane or axis.

15 Claims, 7 Drawing Sheets

(58) Field of Classification Search
CPC .......... A61B 2034/2055; A61B 17/142; A61B 17/1675; B25J 15/0019; B25J 9/10; B25J 9/1633
See application file for complete search history.

(56) References Cited

U.S. PATENT DOCUMENTS

| | | | | |
|---|---|---|---|---|
| 6,728,599 | B2* | 4/2004 | Wang | A61B 34/70 600/595 |
| 6,839,612 | B2* | 1/2005 | Sanchez | A61B 34/37 606/1 |
| 6,999,852 | B2* | 2/2006 | Green | H04N 13/239 600/595 |
| 7,155,316 | B2* | 12/2006 | Sutherland | A61B 34/37 901/1 |
| 7,386,365 | B2* | 6/2008 | Nixon | A61B 34/37 606/139 |
| 2014/0039517 | A1 | 2/2014 | Bowling et al. | |
| 2014/0180290 | A1 | 6/2014 | Otto et al. | |
| 2018/0168750 | A1 | 6/2018 | Staunton et al. | |
| 2018/0325610 | A1 | 11/2018 | Cameron et al. | |
| 2019/0090966 | A1 | 3/2019 | Kang et al. | |
| 2022/0218422 | A1* | 7/2022 | Khurana | A61B 34/20 |
| 2022/0250242 | A1* | 8/2022 | Suresh | B25J 9/1664 |
| 2022/0287782 | A1* | 9/2022 | Shelton, IV | A61B 17/34 |
| 2022/0313366 | A1* | 10/2022 | Finley | A61B 34/25 |
| 2022/0330954 | A1* | 10/2022 | Cameron | A61B 90/11 |

OTHER PUBLICATIONS

Navkar et al., A Framework for Integrating Real-Time MRI With Robot Control: Application to Simulated Transapical Cardiac Interventions, 2012, IEEE, p. 1023-1033 (Year: 2012).*

Patel et al., Body-Mounted Robot for Image-Guided Percutaneous Interventions: Mechanical Design and Preliminary Accuracy Evaluation, 2018, IEEE, p. 1443-1448 (Year: 2018).*

Li et al., Robotic System for MRI-Guided Stereotactic Neurosurgery, 2015, IEEE, p. 1077-1088 (Year: 2015).*

* cited by examiner

SURGICAL SYSTEM AND METHOD FOR TRIGGERING A POSITION CHANGE OF A ROBOTIC DEVICE

CROSS-REFERENCE TO RELATED APPLICATIONS

This application claims priority under 35 U.S.C. § 119 to European Application No. 19212185.3, filed Nov. 28, 2019, which is incorporated herein by reference in its entirety.

TECHNICAL FIELD

The present disclosure relates to a surgical system comprising a robotic device and a method for triggering a position change of such a robotic device.

TECHNICAL BACKGROUND

Some surgical procedures require carrying out a plurality of steps wherein an anatomical structure is treated.

For example, total knee arthroplasty typically requires cutting both the femoral epiphysis and tibial epiphysis in order to remove the damaged bone and cartilage and install a knee prosthesis. To that end, a surgeon has to carry out five or more cuts on the femur and one or more cuts on the tibia by using an oscillating saw through cutting blocks.

FIG. 1 is a schematic perspective view of a knee intended to receive a knee prosthesis including a femoral component FC and a tibial component TC. Generally, the cuts to be made on the femur F are: a distal cut along plane F1, an anterior cut along plane F2, a posterior cut along plane F3, and anterior and posterior chamfers F4, F5 connecting the distal plane and the anterior, respectively posterior, plane. A cut has to be made on the tibia T along plane T1.

In order for the surgeon to carry out all these planes accurately and in a reduced time, robotic systems have been developed.

For example, document WO 2018/103945 teaches a robotic system which comprises a motorized actuation unit, a planar mechanism with a first end attached to a terminal segment of the actuation unit, a second end rigidly attached to an end-effector which is a saw. The saw comprises a body, a saw blade movable relative to the body, and a handle configured to be held by the surgeon to perform the cut. The robotic system also comprises trackers (not shown) respectively attached to the saw and to the patient to determine in real time a relative position of the saw and the bone to be cut, and a control unit configured to compensate small movements from the patient or the surgeon, in order to maintain alignment of the saw blade with a determined plane according to which a cut has to be carried out. FIGS. 2A-2F show perspective views of such a robotic device 1 while carrying out the tibial cut, the distal cut, the anterior cut, the posterior cut, the anterior chamfer cut and the posterior chamfer cut, respectively.

The control of the end effector position for carrying out each cutting step may typically be defined as a sequence of the three followings steps, that are executed in a loop:

stage 1: the robotic device maintains the cutting position prior to and during the cut; the robotic device is not supposed to deviate from the desired cutting position as long as the bone cutting is not complete;

stage 2: the cut is complete; the robotic device is waiting for an instruction to move to the next cutting position; meanwhile, generally, the robotic device maintains the end effector position at the previous cutting position;

stage 3: after receiving an instruction, generally from the user for safety reasons, the robotic device displaces the end effector to the next cutting position.

In order to trigger a change from stage 2 to stage 3, the user may have to use a footswitch, buttons provided on the end effector or on the robotic device, or a virtual button integrated in a software Graphical User Interface and displayed on a touch screen.

This triggering step may require the user to search the footswitch in a non-visible zone, remove his/her hands from the end effector, and/or instruct another person to activate the robotic device, which takes time, interrupts the user's workflow and may be frustrating for the user.

SUMMARY OF THE DISCLOSURE

It is thus desirable to determine a system and a method for triggering a position change of the robotic device which is more ergonomic for the user.

Embodiments relate to a surgical system for treating an anatomical structure according to a plurality of target planes and/or axes, comprising:
  a robotic device comprising:
    an end effector defining a current plane or axis,
    an actuation unit coupled to the end effector,
  a tracking unit configured to determine a pose of the current plane or axis,
  a control unit coupled to the tracking unit and configured to control the actuation unit to align the current plane or axis of the end effector with each one of the plurality of target planes and/or axes to treat the anatomical structure,
  the robotic device being operable in at least the following modes:
    a working mode wherein a treatment is being performed with the end effector constrained to one target plane or axis by the actuation unit, and
    a waiting mode wherein no treatment is being performed and the actuation unit is operable to move the end effector in alignment with another target plane or axis,
  wherein the control unit is further configured to:
  (a) determine that the robotic device is in the waiting mode;
  (b) detect a triggering force applied to the end effector and/or the actuation unit in at least one first direction;
  (c) as a result of determination (a) and detection (b), trigger a position change of the end effector by the actuation unit to align the current plane or axis with a next target plane or axis.

Thanks to said system, the triggering step is made easier and faster since the user can apply the triggering force directly onto the robotic device which is in front of him/her.

In some embodiments, the end effector comprises at least one of: a cutting tool, such as a saw, a burr or a drill, a cutting guide and a guiding tool.

In some embodiments, the tracking unit comprises a tracker rigidly attached to the end effector and/or the actuation unit.

Embodiments relate to a method for triggering a position change of a robotic device for treating an anatomical structure according to a plurality of target planes and/or axes, the robotic device comprising an end effector defining a current plane or axis and an actuation unit coupled to the end effector, the robotic system being operable in at least the following modes:

a working mode wherein a treatment is being performed with the end effector constrained to one target plane or axis by the actuation unit, and a waiting mode wherein no treatment is being performed and the actuation unit is operable to move the end effector in alignment with another target plane or axis, the method comprising:

(a) determining that the robotic device is in the waiting mode;

(b) detecting a triggering force applied to the end effector and/or the actuation unit in at least one first direction;

(c) triggering a position change of the end effector by the actuation unit to bring the end effector in alignment with a next target plane or axis as a result of the determination and detection carried out in steps (a) and (b).

The triggering force may comprise at least one of a linear force and a torque.

In some embodiments, step (b) comprises sensing a value of electrical current in at least one servomotor of the actuation unit greater than a first threshold value.

In some embodiments, step (b) comprises sensing a displacement of the end effector greater than a second threshold value. Said displacement of the end effector may be sensed based on tracking data of the tracking unit.

In some embodiments, step (b) comprises detecting a sequence of external linear forces and/or torques applied to the end effector and/or the actuation unit.

In some embodiments, the end effector comprises a powered tool including a trigger, and step (b) further comprises detecting a pressure exerted onto the trigger while the tool is in OFF state.

In some embodiments, the position change of the end effector is implemented substantially according to the first direction.

In some embodiments, the method may comprise stopping a triggered movement of the robotic device as a result of the detection of an external force different from the triggering force.

In some embodiments, step (a) comprises determining a position of the end effector relative to the anatomical structure using a medical image and/or anatomical landmarks.

In some embodiments, step (b) further comprises sensing a duration of application of the external force and comparing said sensed duration with a duration threshold.

In some embodiments, in step (c) the control unit triggers a displacement of the end effector (2) by a determined offset amplitude in the first direction and said offset is cancelled upon release of the triggering force.

BRIEF DESCRIPTION OF THE FIGURES

Further embodiments and advantages will be described in the following detailed description, with reference to appended drawings wherein.

DETAILED DESCRIPTION OF EMBODIMENTS

Figure 1:
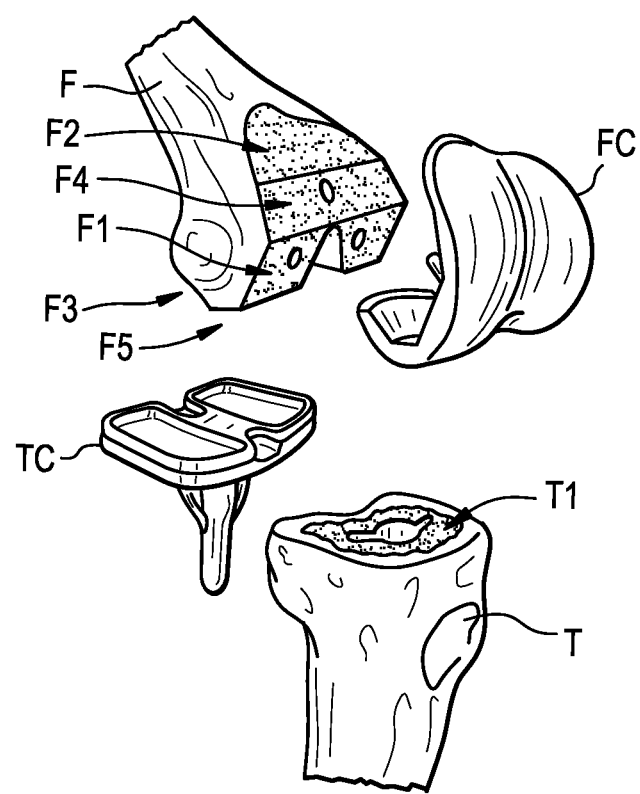
FIG. 1 schematically illustrates the cuts to be made into a femur and a tibia in order to implant a knee prosthesis.
Figure 2A:
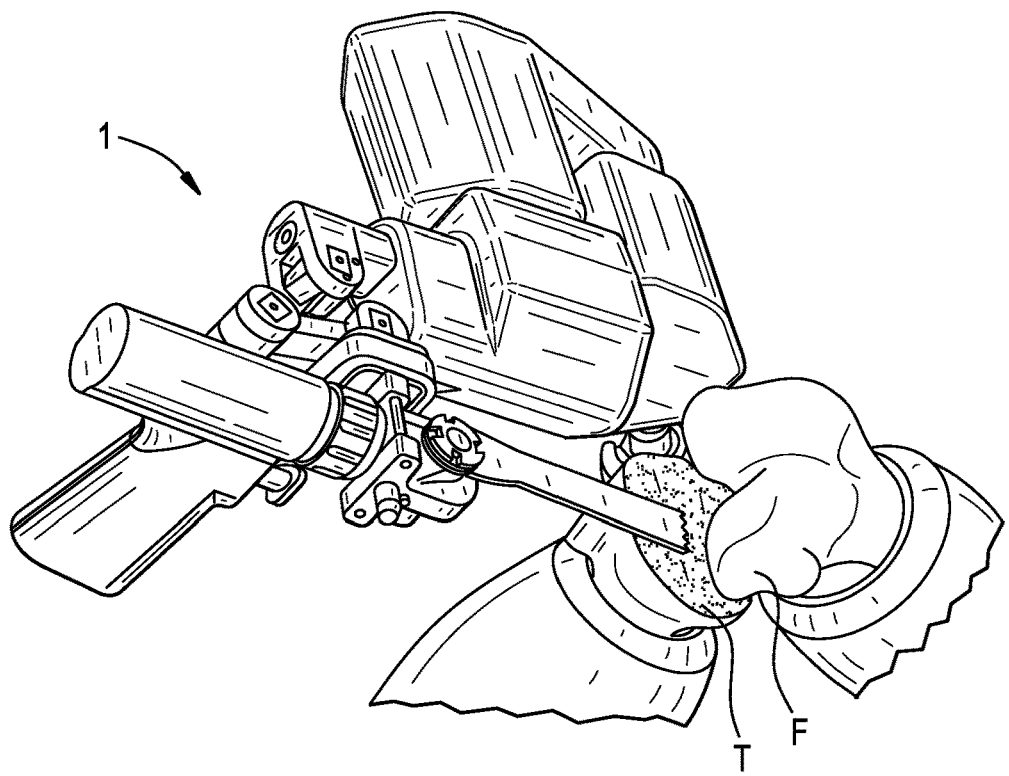
FIGS. 2A-2F show perspective views of a robotic device carrying out the tibial cut, the distal cut, the anterior cut, the posterior cut, the anterior chamfer cut and the posterior chamfer cut, respectively.
Figure 2B:
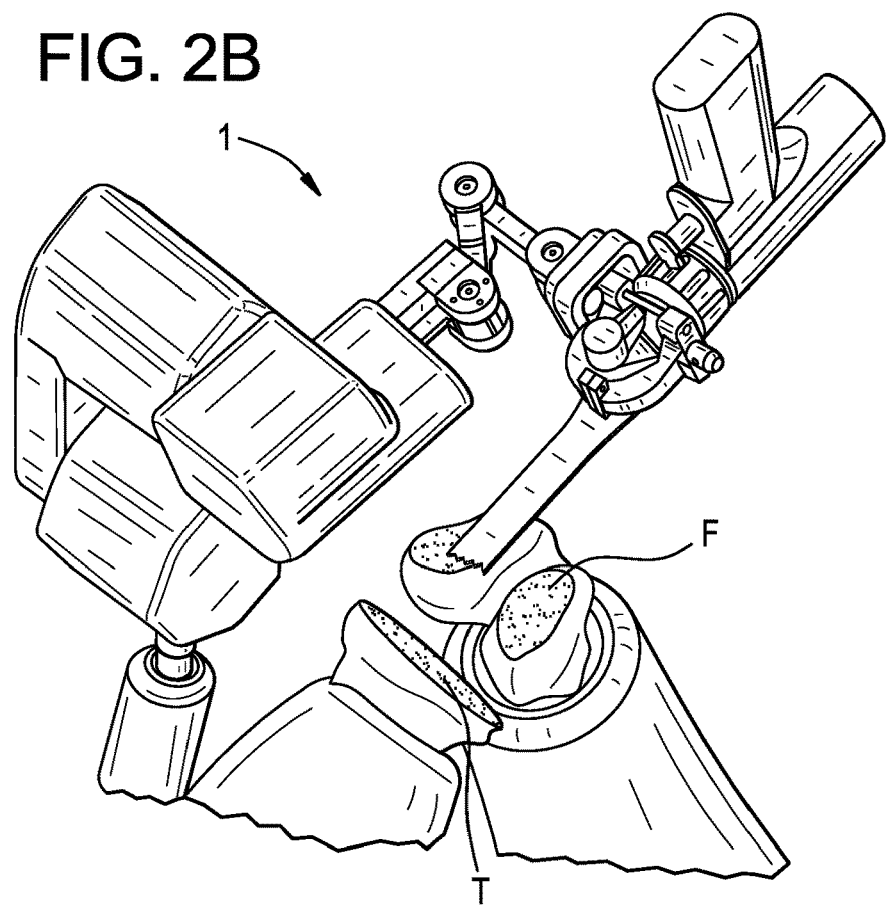
Figure 2C:
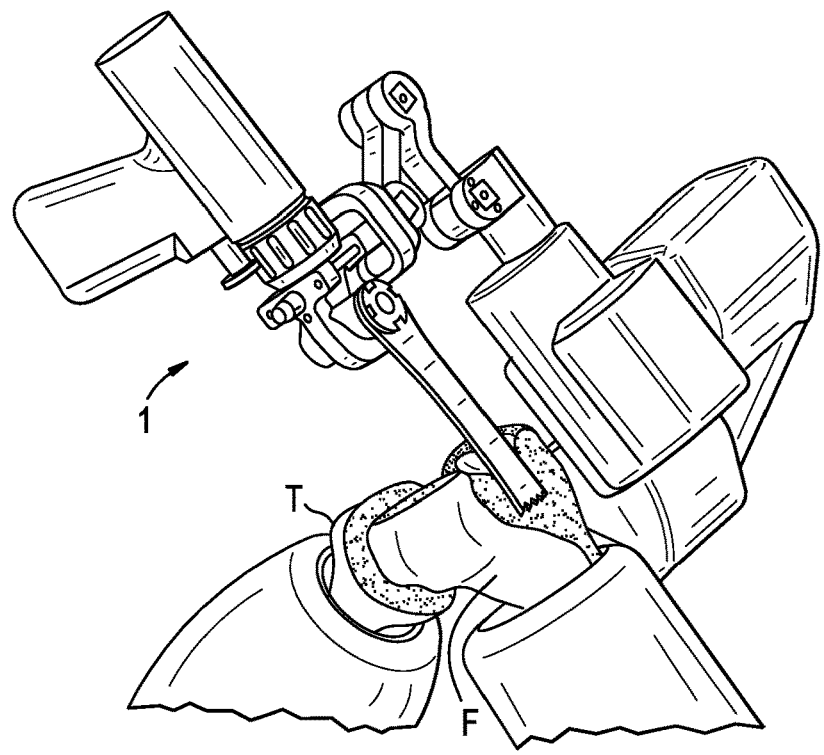
Figure 2D:
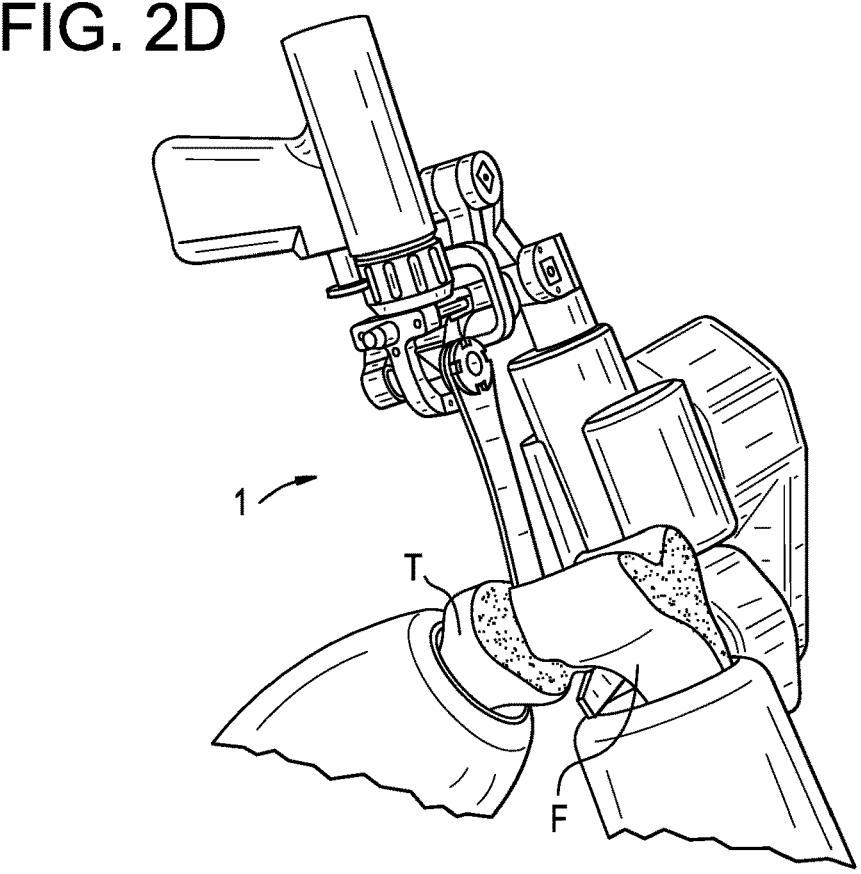
Figure 2E:
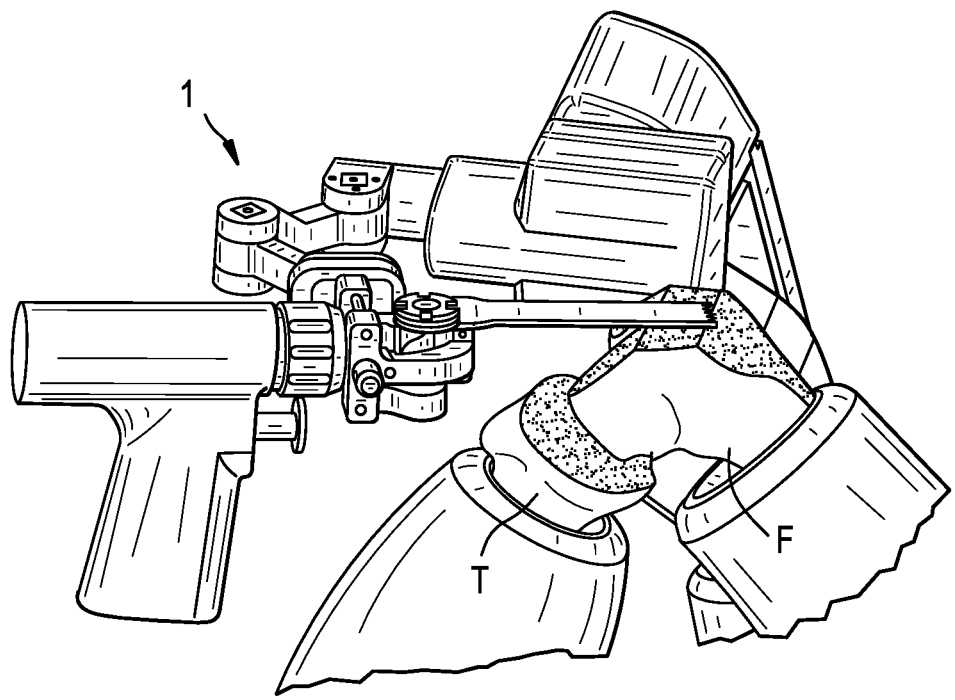
Figure 2F:
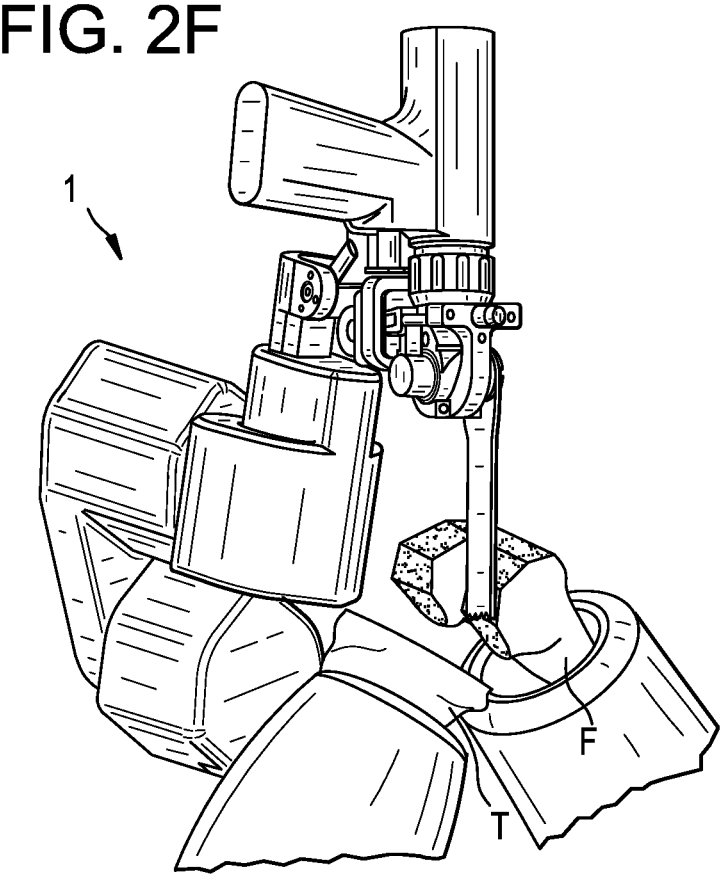

The robotic device comprises a base, an end effector defining a current plane or axis, and a motorized actuation unit coupled to the end effector to move the end effector relative to the base.

In some embodiments, the end effector may be a bone cutting tool, such as a saw, a burr or a drill. If the tool is a surgical saw, the end effector defines a current plane which is the plane in which the saw blade oscillates. If the tool is a burr or a drill, the end effector defines a current axis which is the longitudinal axis of the burr or the drill.

In other embodiments, the end effector may comprise a cutting guide, which is a rigid block comprising at least one through aperture in the form of a slot (defining a current plane) or a cylindrical hole (defining a current axis) configured to guide a bone cutting tool which is freely movable by a user according to the current plane or axis.

In other embodiments, the end effector may comprise a guiding tool for guiding an implant inserting tool, such as an implant impactor or a screw driver, according to a current axis.

In some embodiments, the end effector may be connected to the actuation unit by a planar mechanism which is configured to constrain the movement of the cutting tool within the cutting plane.

Advantageously, the cutting tool can be decoupled from the planar mechanism. Preferably, especially in the case where the cutting tool is not intended to receive a tracker, the attachment means for the cutting tool provides reproducible fixation.

Several different architectures exist to implement a planar mechanism. For example, the planar mechanism can be made of only one rotation axis and then one translation axis that carries the cutting tool along its longitudinal direction. Alternatively, the planar mechanism can be made of two orthogonal translation axes and then a rotational axis. According to another embodiment, the planar mechanism can be a slider in the form of an arch, including a rotation axis, and then a translation axis that carries the cutting tool.

According to an embodiment, the planar mechanism is passive, meaning that the mechanism is not motorized and can be freely manipulated by the user. One advantage of such a passive mechanism is to preserve all the perceptions of the user when the saw is manipulated in the bone. For example, surgeons are used to freely manipulate a saw in a cutting block and to detect when the saw blade has reached the back of the bone by sensing changes in the bone resistance, and this perception is fully preserved with a passive planar mechanism that has very low friction at its joints.

Alternatively, the planar mechanism may also be at least partially active, i.e. comprising at least one motorized degree of freedom. If the planar mechanism is active, i.e. it comprises at least two motorized degrees of freedom, the cut(s) can be performed automatically. It is to be noted that said motorized degrees of freedom are all configured to move the cutting tool within the cutting plane.

Whatever the embodiment, the planar mechanism may comprise a locking system for locking each of its degrees of freedom once the cutting plane has been aligned with the target plane.

The actuation unit may have a serial architecture made of a plurality of mobile segments. In some embodiments, the actuation unit has three motorized rotational degrees of freedom for adjusting the position and orientation of the cutting plane relative to each target plane. In other embodiments, the actuation unit has two motorized rotational degrees of freedom and one or two motorized translational degrees of freedom. Generally speaking, the actuation unit comprises from three to five motorized degrees of freedom, at least two of which being rotational degrees of freedom orthogonal to each other. The segments and their components are integrated in an optimal way such that the robotic device remains as compact and light as possible while remaining strong enough to be able to hold the planar mechanism and the surgical tool, as well as resisting to some normal pressure applied by the user when he/she manipulates the surgical tool.

In some embodiments, the architecture of the actuation unit is made of three rotational degrees of freedom.

In some embodiments, the segments are arranged such that the first and third rotation axes are substantially parallel to each other and the second axis is substantially orthogonal to the first and third axes.

In other embodiments, either the first and second axes or the second and third axes are substantially parallel to each other, and the first axis is substantially orthogonal to the third axis.

In use for knee arthroplasty (TKA, UKA, etc.), the robotic device may be placed on the medial (internal) or on the lateral (external) side of the leg of interest. The first rotation axis is intended to be substantially orthogonal to the sagittal plane of the knee. For any application of the robotic system, it is possible to define some anatomical landmarks that are easy to identify and to use them for aligning the actuation unit in a ball park.

In some embodiments, the architecture of the actuation unit may enable additional movements—which can be motorized or not—within the cutting plane.

As it will be explained in more details below, the actuation unit is controlled by the control unit. The control unit may be integrated in the robotic device, or remote from the robotic device.

The system may comprise an articulated lockable holding arm supporting the base of the robotic device and suited to be connected to a mechanical support such as an operating table, a leg holder or mounted on a mobile cart which wheels can be blocked. A leg holder is an adjustable mechanism configured to maintain the leg in a given flexed position when the patient lies on the operating table.

The holding arm may be made of several articulated segments using ball-and-socket joints, rotational and/or translational joints.

The holding arm is lockable, either manually by a knob (mechanical locking system) or actively by a dedicated actuator of a locking system. The locking system may be an electrical system, a piezoelectric system, a hydraulic system, a pneumatic system or a combination of such systems (e.g. a hydraulic cylinder driven by an electric motor). For example, company SMITH & NEPHEW sells a passive holding arm, actively lockable, named SPIDER™. The actuator can be a button, a foot switch, a remote button, etc. To manipulate the robotic device, the user has to maintain the actuator activated until the desired pose of the robotic device has been achieved.

The holding arm supports the weight of the robotic device and maintains it in a rough positioning relative to the anatomical structure to be treated. It limits the movements of the user when operating the device—and, in advantageous embodiments, also damps movements of the user and/or the patient, vibrations of the cutting tool and reaction forces caused by movements of the actuation unit.

According to an embodiment, the holding arm is passive. Advantageously, the holding arm may be braked progressively depending on the distance between the robotic device and a target position of the robotic device relative to a tracker fixed to the patient. For example, the braking force may be inversely proportional to the distance of the robotic device to its target position. Alternatively, one or several concentric volumes (e.g. cubes or spheres) may be defined around the target position of the robotic device. The braking force may adjust depending on the presence of the robotic device in one of said volumes. Thus, when the robotic device is close to the target position, the holding arm is braked and the user may receive a force-feedback information. Alternatively, feedback information may be provided in the form of a light or acoustic signal. For example, a variable flash frequency and/or intensity of a light signal may indicate the distance between the robotic device and its target position. Similarly, a variable frequency, repeat speed and/or amplitude of an acoustic signal may indicate such a distance. In any case, the braking is not full, so that the user is always able to manipulate the robotic device until its final desired position. The holding arm is then locked upon an action from the user (e.g. by operating the actuator, e.g. releasing or pushing a button). If the user wants to move the robotic device again, he/she has to operate the actuator again, which frees the holding arm—possibly with a braking force as described above. If a new target position of the robotic device is defined, new braking volumes are defined, and the braking is adjusted based on said new volumes.

Preferably, the connection between the holding arm and the actuation unit is as close as possible to the first segment of the actuation unit or to the center of gravity of the robotic device in order to minimize any lever-arm effect. The part of the actuation unit that is attached to the holding arm is called the base of the robotic device.

According to an embodiment, the base of the robotic device may be fixed relative to the holding arm. This architecture is advantageous in that it minimizes the weight of the moving components of the actuation unit. As a result, the robotic device may be more responsive, which is favorable to real time control of the cutting plane or axis.

The system further comprises a tracking unit configured to determine in real time the pose of the saw with respect to the anatomical structure to be cut.

The tracking unit may typically comprise a tracking system, which is known per se.

Tracking systems commonly used in computer-assisted surgery use a variety of different technologies (passive optical, active optical, electromagnetic, inertia with gyroscopic measurements, ultrasonic, etc.) that can be used individually or in combination. According to a preferred embodiment, the tracking system is based on passive optical technology.

The tracking unit comprises at least one tracker that may be attached to any component of the actuation unit, e.g. to one of the mobile segments.

The position of each segment of the actuation unit is known in real time thanks to encoders or sensors of the servomotors, and a calibrated model of the robotic device that includes all axes and distances of the segments of the actuation unit. Using this model, and well-known geometric modeling techniques in robotics, it is possible to calculate the relative positions of all segments, so if one measurement is known in a coordinate system attached to the base of the robotic device using an external tracker, then any segment position is also known in the same coordinate system. Additionally, if a tracker is attached to the base of the actuation unit and a second tracker is attached to the anatomical structure, then the pose of any segment of the actuation unit is known in the coordinate system attached to the tracker of the anatomical structure.

The control unit is coupled to the tracking unit and configured to control the actuation unit to align the current plane or axis of the end effector with each one of the plurality of target planes and/or axes to treat the anatomical structure.

Figure 3:
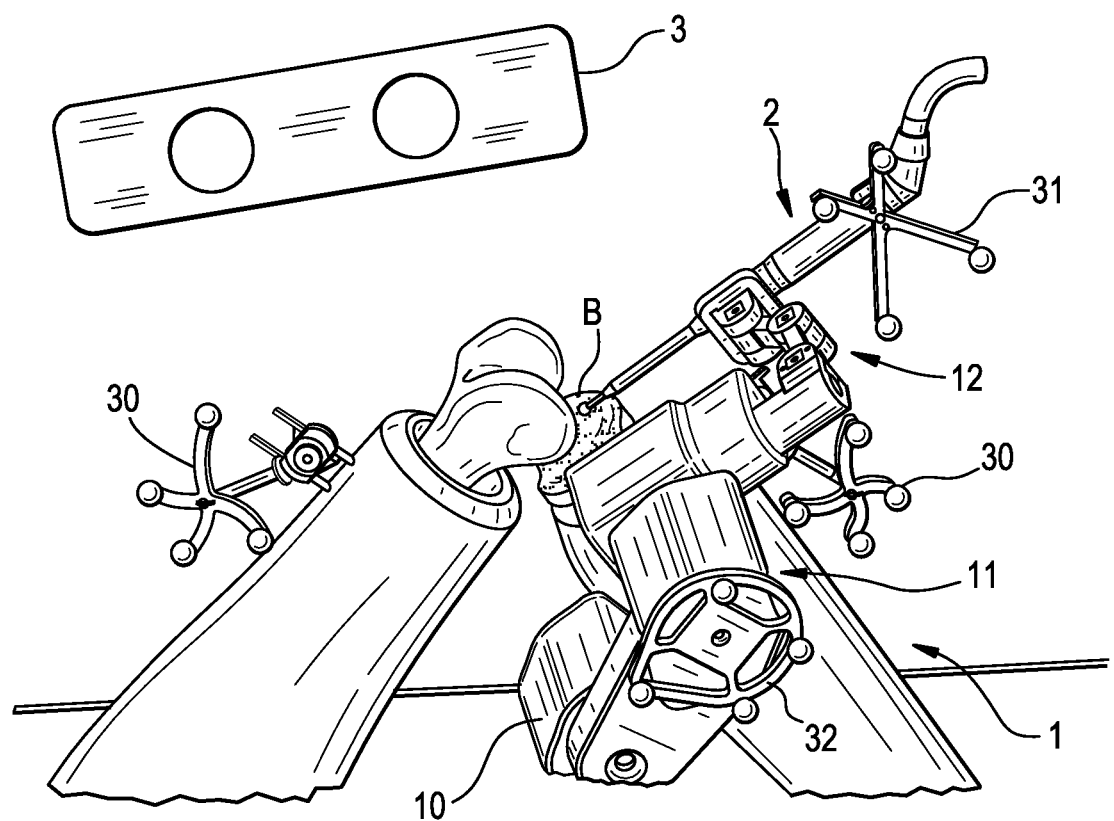
FIG. 3 is a perspective view of a surgical system according to an embodiment.

FIG. 3 shows a general overview of the surgical system. In the illustrated embodiment of the robotic device, the end effector 2 comprises a burr. However, the other components of the system may be used with other end effectors as mentioned above.

The robotic device 1 comprises a base 10, a motorized actuation unit 11, and an end effector 2 which is a surgical burr. The burr is coupled to the actuation unit by a planar mechanism 12, with a first end attached to a terminal segment of the actuation unit, and a second end rigidly attached to the burr 2.

Especially if the burr head is small (e.g. with a diameter of the order of three mm), the operation of the burr constrained in a cutting plane allows performing a planar cut. The burr tip can be spherical or cylindrical. Typically a cylindrical shape burr tip with a three mm diameter constrained by the planar mechanism to remain in a plane parallel to the cylinder axis is rigid enough to make large cuts and small enough to perform fast cutting.

The base 10 may be attached to a lockable holding arm (not illustrated in FIG. 3).

A tracker 30 is attached to the bone B to be cut.

A tracker 31 is attached to the end effector 2 and another tracker 32 is attached to the base 10 of the robotic device to determine in real time a relative position of the end effector and the bone to be cut.

In the illustrated embodiment, the trackers 30, 31, 32 are optical trackers and are tracked by a localization camera 3. In other embodiments, the trackers could be electromagnetic trackers, tracked by an electromagnetic tracking unit.

A control unit (not shown) controls the actuation unit to maintain the current axis of the burr along a target axis to compensate in real time small movements from the patient or the surgeon.

The tracker 32 attached to the base 10 may be sufficient to control the robotic device, since a model of the robotic device and the positions of the servomotors of the actuation unit are known, but the tracker 31 attached to the end effector provides additional information about the position and orientation of the burr.

Figure 4:
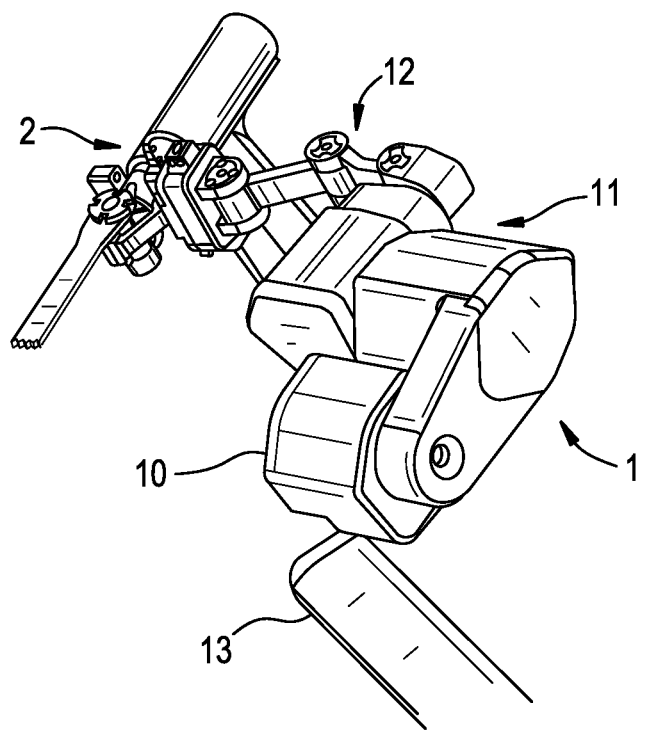
FIG. 4 is a perspective view of a robotic device according to an embodiment.

FIG. 4 shows another embodiment of the robotic device, wherein the end effector comprises a saw. The elements designated by the same references as the elements of FIG. 3 fulfill the same function and may thus not be described again.

The robotic device 1 comprises a base 10, a motorized actuation unit 11 and an end effector 2 which is a surgical saw. The saw is connected to the actuation unit 11 by a planar mechanism 12.

The base 10 is rigidly attached at an end of a lockable holding arm 13. The opposite end of the arm 13, which is not visible in FIG. 4, may be rigidly attached to an operating table or to a cart placed in the vicinity of the operating table.

Although not illustrated, trackers (e.g. optical or electromagnetic trackers) are attached to the anatomical structure of the patient and to the robotic device (e.g. to the base and advantageously also to the end effector).

Figure 5:
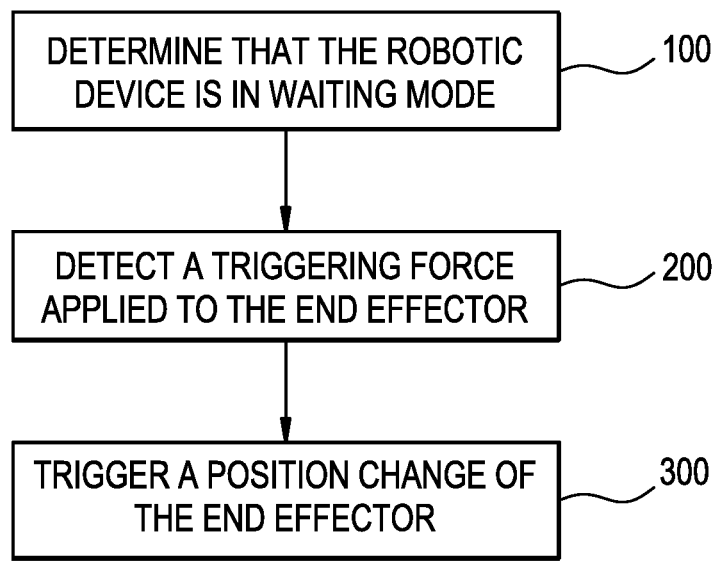
FIG. 5 illustrates a flowchart of a method for triggering a position change of the robotic device.

FIG. 5 is a flowchart illustrating an embodiment of the method implemented by the control unit.

Before implementing said method, a plurality of target planes or axes may be planned by a user. This planning step may be done by techniques that are known per se and will not be described in the present text. Usually, the user determines not only the position and orientation of each target plane or axis with respect to the anatomical structure but also the order of the cuts to be carried out. The planning may thus comprise a sequence of at least two cuts according to different target planes or axes to be made in a determined order. The planning may be generated by the control unit itself or may be generated by another device and transferred to the control unit.

For safety reasons, the end effector cannot be moved to another position as a cut is being performed.

Thus, in a first step (step 100), the control unit has to determine that the robotic device is waiting for an instruction to bring the end effector in alignment with a target plane or axis (waiting mode).

This determination may be made by various techniques, which may possibly be combined.

For example, if the end effector is a powered tool (e.g. a surgical saw, a drill or a burr), the tool being in an OFF state may be an indication that the previous cutting step has been achieved and that the end effector has to be brought in alignment with the next target plane or axis. Indeed, the end effector cannot be moved while the treatment is being performed (working mode).

However, this OFF state alone may not be sufficient and may be supplemented by another information, such as the computation of the completeness of the cut by an algorithm implemented by the control unit. Said computation may for example be based on bone geometry and the path or the position of the end effector.

Another possibility is to determine the position of the end effector relative to the anatomical structure, using a medical image and/or anatomical landmarks. Indeed, when a cut is finished, the user or the robotic device may retract the end effector from the bone to wait for the next cut to be done. A given distance between the end effector and the anatomical structure may thus be indicative of a waiting state of the robotic device.

Thanks to localization data of the anatomical structure and of the end effector provided by the tracker, the control unit may compute a distance between the surface of the anatomical structure and the end effector.

If a medical image of the anatomical structure is available, it may also be possible to determine a distance between the surface of the anatomical structure and the end effector from a treatment of the image. Said medical image may be a preoperative 3D image (e.g. a CT scan or an MRI image), used to navigate the end effector. Alternatively, said medical image may be a 2D or 3D intraoperative image.

In an imageless system, intraoperative acquisition of anatomical landmarks by a pointer tracker by the tracking unit may also allow determining a distance between the surface of the anatomical structure and the end effector.

In a second step (step 200), the control unit has to detect an external force applied to the end effector or the actuation unit in at least one first direction. The force may also be applied to the planar mechanism if any. More generally, the force may be applied to any part of the robotic device which is not rigidly linked to the holding arm.

Such an external force may be applied by a user onto the end effector to indicate that a position change is desired.

Said external force (also called "triggering force" in the present text) may be in the form of a linear force and/or a torque.

For safety reasons, it may be preferable that the triggering force combines at least one linear force and at least one torque, or at least two linear forces according to different directions or according to a same direction within a given timeframe, or at least two torques along different directions or along a same direction within a given timeframe. Otherwise said, the triggering force may combine at least two forces or torques according to a predetermined sequence. A sequence may preferably be defined by predetermined space parameters (e.g. a direction or a plurality of directions) and time parameters (e.g. a duration of application of a force or torque and/or a time period between application of successive forces or torques), which together constitute a predetermined signal that will be interpreted by the control unit as an order to move the end effector to a new position. In this way, the risk to trigger an undesired position change may be minimized.

Preferably, said sequence may be designed so as to unlikely be happen involuntarily. For example, the sequence may comprise at least one positive torque and one negative torque successively applied to the end effector in a first direction. Alternatively, the sequence may comprise at least one torque exerted around a first axis and one force exerted along a second axis perpendicular to the first axis. In yet another example, a force may be applied to the actuation unit and the end effector may be waved back and forth with a large amplitude thanks to the planar mechanism.

The detection of the triggering force may be done by several techniques, which may be combined. These techniques generally involve components already present in the system.

In some embodiments, the detection of the triggering force may be done by sensing a value of electric current in the at least one servomotor greater than a first threshold value. Indeed, application of an external force onto the actuation unit or end effector results in generation of a force or torque by at least one servomotor to act under the exerted force and maintain the end effector in the current waiting position. The force or torque applied by the servomotor results in an increase in electric current consumption in the servomotor. Said electric current may be measured (in Ampere) by sensors of the servomotor, of the control unit and/or of a unit powering the servomotors.

Depending on the direction of the external force applied to the actuation unit or the end effector, the electric current may increase in one or several motors of the actuation unit. A specific threshold value may be defined for each concerned servomotor.

Advantageously, directions in which a triggering force is expected may be monitored more finely, e.g. by requiring a smaller threshold value for the servomotor(s) capable of exerting a counter-force or torque in these directions.

In some embodiments, the detection of the triggering force may be done by sensing a displacement of the end effector greater than a second threshold value.

Said displacement may be sensed based on tracking data using the tracker attached to the end effector.

Advantageously, directions in which a triggering force is expected may be monitored more finely, e.g. by requiring a smaller displacement threshold value in these directions.

In addition to the direction of the force exerted by the user, the detection may also include sensing the duration of application of the triggering force and detecting the triggering force only if said duration is above a third threshold value. This is intended to avoid that a movement of the end effector to a new position be triggered by a shock or an unintentional pressure exerted to the end effector or the actuation unit.

To that end, the control unit may include a timer which is triggered by the detection of a first event which is potentially representative of the expected signal. For example, the external force may have to be sufficiently long to trigger a movement of the robotic device. In that case, the control unit may trigger the timer as soon as the electric current of a given servomotor is above the first threshold and detect that the applied force belongs to the signal if the electric current remains greater than the first threshold value during a duration greater than the third threshold value. In some embodiments, the triggering force may be a sequence of different individual forces exerted in a same or in different directions. In that case, the control unit may determine the duration of each individual force and check whether each duration is within a given range.

In case the triggering force to be detected is a combination of individual forces or torques, the time period between the application of successive individual forces or torques may also be measured and compared with a predetermined range. The control unit may thus detect the triggering force only if the time period between successive applications of individual forces or torques is within said predetermined range.

As mentioned above, the detection techniques described above may be combined. For example, the user may first wave the end effector according to a determined pattern (e.g. left/right or right/left) thanks to the planar mechanism. This movement puts the control unit in alert; the control unit may trigger a timer to measure the time period between this first event and a next event in the form of an applied triggering force. The user may thus apply said force onto the end effector or the actuation unit in a determined direction, which will be detected by the control unit.

In some embodiments, the control unit and robotic device may be configured to provide a "push-button" feeling to the user. In that case, the application of the triggering force in the first direction may cause the control unit to trigger a displacement of the end effector by a determined amplitude in the first direction, which generates an offset of the end effector relative to its initial position. For example, if a linear force is being applied by the user, the end effector may typically translate by 1 to 10 mm; if a torque is being applied by the user, the end effector may rotate by 0.5 to 5°. Said offset of the end effector may be cancelled upon release of the triggering force.

Said "push-button" effect may be short, in so far as either the displacement of the end effector starts only once the triggering force is released by the user, or the displacement starts when the triggering force is applied and then the triggering force can be released any time after the movement has started. The effect may also be long, in so far as the displacement of the end effector starts and continues as long as the user applies the triggering force. In the latter case, during said displacement, the instantaneous position of the end effector is at an offset compared to the position it would have if this "push-button" action was not used. Once the triggering force is released, said offset is cancelled.

The force applied to the end effector and/or actuation unit may not be the sole parameter taken into account in the detection step. For example, if the end effector is a powered tool, the detection of the triggering force may be combined with the detection that a user presses on the trigger of the tool. If the robotic device is in waiting state, pressing the trigger may not activate the tool, but it may generate an electrical signal detectable by the control unit. The combined detection of a triggering force exerted onto the end effector and/or actuation unit in a given direction and of an electrical signal in the trigger of the powered tool may thus be interpreted as the required signal.

As a result of the first and second detection steps, the control unit triggers a position change of the end effector by the actuation unit to align the current plane or axis with a next target plane or axis (step 300).

In some embodiments, the next target plane or axis may be the spatially closest to the current plane or axis, meaning the plane or axis requiring the smallest displacement from the current position of the end effector. Said smallest displacement may be considered in the direction of application of the triggering force.

In other embodiments, the next target plane or axis may be the next or previous plane or axis according to the planned surgical workflow. It may be necessary to go back to the previous target plane or axis if the cut has to be redone or improved, for example. Advantageously, the direction with respect to the planned workflow (i.e. to the next or to the previous target plane or axis) may be indicated by opposite directions of the triggering force. For example, a force exerted upwards may trigger a transition to the next step in the planned workflow, and a force exerted downwards may trigger a transition to the previous step in the planned workflow.

In some embodiments, an external force—or a sequence of forces and/or torques—, different from the triggering force may be used to stop movement of the end effector, e.g. to cancel a signal previously detected by the control unit.

Advantageously, the control unit is configured to record the status of a given cutting step. Otherwise said, the control unit may be able to determine whether a cut according to a given plane or axis has already been performed or not.

For example, at the end of the anterior cut that has been performed, the user may want to come back to the distal cut to check the plane with the saw blade. In this case, the robotic device will stay in the waiting mode when the robot is on the distal plane again as this cut has already been performed. If the user just wanted to check the performed cut with the saw blade, he can then directly apply a triggering force so that the robotic device moves to the next cut without performing the cut again.

Although the previous description was focused on robotic devices with less than six degrees of freedom—which distinguish over large surgical robots by a lower inertia especially according to the first axis and thus a greater responsiveness required in particular to compensate for bone motion in real time—the present disclosure is also applicable to surgical robots having six degrees of freedom. Indeed, these robots also integrate servomotors or other means allowing detecting application of a triggering force onto the robot or the end effector and a control unit which may be configured to trigger a position change of the end effector in response to such a triggering force.

REFERENCES

WO 2018/103945

The invention claimed is:

1. A surgical system for treating an anatomical structure according to a plurality of target planes and/or axes, comprising:
   a robotic device comprising:
   an end effector defining a current plane or axis,
   an actuation unit coupled to the end effector,
   a tracking unit configured to determine a pose of the current plane or axis-,
   a control unit coupled to the tracking unit and configured to control the actuation unit to align the current plane or axis of the end effector with each one of the plurality of target planes and/or axes to treat the anatomical structure,
   the robotic device being operable in at least the following modes:
      a working mode wherein a treatment is being performed with the end effector constrained to one target plane or axis by the actuation unit, -and
      a waiting mode wherein no treatment is being performed and the actuation unit is operable to move the end effector in alignment with another target plane or axis,
   wherein the control unit is further configured to:
      (a) determine that the robotic device is in the waiting mode;
      (b) detect a triggering force applied to the end effector or the actuation unit in at least one first direction;
      (c) as a result of determination (a) and detection (b), trigger a position change of the end effector by the actuation unit to align the current plane or axis with a next target plane or axis.

2. The surgical system according to claim 1, wherein the end effector comprises at least one of: a cutting tool, such as a saw, a burr or a drill, a cutting guide and a guiding tool.

3. The surgical system according to claim 1, wherein the tracking unit comprises a tracker rigidly attached to the end effector or the actuation unit.

4. A method for triggering a position change of a robotic device for treating an anatomical structure according to a plurality of target planes and/or axes, the robotic device comprising an end effector defining a current plane or axis and an actuation unit coupled to the end effector, the robotic system being operable in at least the following modes:
   a working mode wherein a treatment is being performed with the end effector constrained to one target plane or axis by the actuation unit, -and
   a waiting mode wherein no treatment is being performed and the actuation unit is operable to move the end effector in alignment with another target plane or axis,
   the method comprising:
      (a) determining that the robotic device is in the waiting mode;
      (b) detecting a triggering force applied to the end effector and/or the actuation unit in at least one first direction;
      (c) triggering a position change of the end effector by the actuation unit to bring the end effector in alignment with a next target plane or axis as a result of the determination and detection carried out in steps (a) and (b).

5. The method according to claim 4, wherein the triggering force comprises at least one of a linear force and a torque.

6. The method according to claim 4, wherein step (b) further comprises sensing a value of electrical current in at least one servomotor of the actuation unit greater than a first threshold value.

7. The method according to claim 6, further comprising sensing a displacement of the end effector greater than a second threshold value.

8. The method according to claim 7, comprising sensing said displacement of the end effector based on tracking data of the tracking unit.

9. The method according to claim 4, wherein step (b) further comprises detecting a sequence of external linear forces or torques applied to the end effector or the actuation unit.

10. The method according to claim 4, wherein the end effector comprises a powered tool including a trigger, and step (b) further comprises detecting a pressure exerted onto the trigger while the tool is in OFF state.

11. The method according to claim 5, wherein the position change of the end effector is implemented substantially according to the first direction.

12. The method according to claim 4, further comprising stopping a triggered movement of the robotic device as a result of the detection of an external force different from the triggering force.

13. The method according to claim 4, wherein step (a) comprises determining a position of the end effector relative to the anatomical structure using a medical image or anatomical landmarks.

14. The method according to claim 4, wherein step (b) further comprises sensing a duration of application of the external force and comparing said sensed duration with a duration threshold.

15. The method according to claim 4, wherein in step (c) the control unit triggers a displacement of the end effector by a determined offset amplitude in the first direction and said offset is cancelled upon release of the triggering force.

* * * * *